(12) United States Patent
Stashenko et al.

(10) Patent No.: US 7,326,733 B2
(45) Date of Patent: Feb. 5, 2008

(54) METHODS FOR INCREASING BONE DENSITY

(75) Inventors: Philip Stashenko, Medfield, MA (US); Richard Battaglino, Boston, MA (US)

(73) Assignee: The Forsyth Institute, Boston, MA (US)

( * ) Notice: Subject to any disclaimer, the term of this patent is extended or adjusted under 35 U.S.C. 154(b) by 128 days.

(21) Appl. No.: 10/453,273

(22) Filed: Jun. 2, 2003

(65) Prior Publication Data

US 2004/0127573 A1 Jul. 1, 2004

Related U.S. Application Data

(60) Provisional application No. 60/385,314, filed on May 31, 2004.

(51) Int. Cl.
*A61K 31/135* (2006.01)

(52) U.S. Cl. ..................................... 514/647

(58) Field of Classification Search ................ 514/179, 514/469, 523, 647, 651
See application file for complete search history.

(56) References Cited

U.S. PATENT DOCUMENTS

| 4,314,081 A | 2/1982 | Molloy et al. ............... 564/347 |
| 4,626,549 A | 12/1986 | Molloy et al. ............... 514/651 |

OTHER PUBLICATIONS

Paul Ullom-Minnich, M.D., "Prevention of Osteoporosis and Fractures", American Family Physician, vol. 60, No. 1, pp. 194-202 (1999).*
M.M. Bliziotes et al., "Neurotransmitter Action in Osteoblasts: Expression of a Functional System for Serotonin Receptor Activation and Reuptake", Bone, vol. 29, No. 5, pp. 477-486 (2001).*
Beers et al., The Merck Manual of Medical Information, Second Home Edition, pp. 341-342 & 343.*
Ader, et al., *Annu. Rev. Pharmacol. Toxicol.*, 30:561-602 (1990).
Azuma, et al., *J. Biol. Chem.*, 275(7):4858-4864 (2000).
Bab, et al., *Crit. Rev. Eukaryot. Gene Expr.*, 3(1):31-46 1993).
Barker, et al., *J. Neurosci.*, 19(12):4705-4717 (1999).
Battaglino, et al., *J. Bone Mineral Res.*, 17(5):763-773 (2002).
Bliziotes, et al., *Bone*, 29(5):477-486 (2001).
Byrd, et al., *J. Dent. Res.*, 80(8):1730-1735 (2001).
Coelho, et al., *J. Psychosom. Res.*, 46(1):29-35 (1999).
Cornea-Hérbert, et al., *J. Comp. Neurol.*, 409(2):187-209 (1999).
De Gennes, et al., *Clin. Orthop.*, 279:281-291 (1992).
Doherty, et al., *Brain Res.*, 864(2):176-185 (2000).
Emanuelsson, et al, *Cell Differ.*, 24(3):191-199 (1988).
English, et al., *Anat. Rec.*, 232(1):112-120 (1992).
Fanslow, et al., *Semin. Immunol.*, 6:267-278 (1994).
Galibert, et al., *J. Biol. Chem.*, 273(51):34120-34127 (1998).
Greenberg, et al., *Am. J. Med. Genet.*, 96(2):202-216 (2000).
Halbreich, et al., *Schizophr. Bull.*, 22(3):447-454 (1996).
Hansson, et al., *Neuroscience*, 89(1):243-265 (1999).
Hayashi, et al., *Biochem. Cell Biol.*, 76(6):911-922 (1998).
Heils, et al., *J. Neurochem.*, 66(6):2621-2624 (1996).
Herrán, et al., *Psychosom. Med.*, 62(6):779-782 (2000).
Kubera, et al., *Polish J. Pharmacol.*, 52(3):229-235 (2000).
Lam, K.S., *Anti-Cancer Drug Des.*, 12(3):145-167 (1997).
Lesclous, et al., *Calcif. Tissue Int.*, 68(5);297-303 (2001).
Licinio, et al., *Mol. Psychiatry*, 4(4):317-327 (1999).
Liu, et al., *Pharmacogenetics*, 9(4):491-495 (1999).
Looker, et al., *Osteoporos. Int.*, 8(5):468-489 (1998).
Lundberg, et al., *Bone*, 27(6):803-810 (2000).
Michelson, et al., *N. Engl. J. Med.*, 335:1176-1181 (1996).
Moisewitsch, et al., *Arch. Oral Biol,*, 43(10):789-800 (1998).
Morse, et al., *Immunity*, 6(1):47-56 (1997).
Mössner, et al., *Brain Behav. Immun.*, 12(4):249-271 (1998).
Müller, et al., *Bone*, 23(1):59-66 (1998).
Owens, et al., *J. Cell. Phisiol.*, 179(2):170-178 (1999).
Reichlin, S., *N. Engl. J. Med.*, 329:1246-1253 (1993).
Schweiger, et al., *Am. J. Psychiatry*, 157(1):118-120 (2000).
Shuey, et al., *Teratology*, 46(4):367-378 (1992).
Smeraldi, et al., *Mol. Psychiatry*, 3(6):508-511 (1998).
Suda, et al., *Methods in Enzymol.*, 282:223-235 (1997).
Suda, et al., *Endocrine Rev.*, 20(3):345-357 (1999).
Takahashi, et al., *Biochem. Biophys. Res. Commun.*, 256(3):449-455 (1999).
Takeshita, et al., *J. Bone Mineral Res.*, 15(8):1477-1488 (2000).
Udagawa, et al., *Bone*, 25(5):517-523 (1999).
Valentijn, et al., *Bone*, 32(3):269-274 (1997).
Westbroek, et al., *J. Biol. Chem.*, 276(31):28961-28968 (2001).
Winding, et al., *Exp. Physiol.*, 82(5):871-886 (1997).

* cited by examiner

*Primary Examiner*—Raymond J. Henley, III
(74) *Attorney, Agent, or Firm*—Mintz, Levin, Cohn, Ferris, Glovsky and Popeo, P.C.; Ingrid A. Beattie

(57) ABSTRACT

Methods and compounds for remodeling bone and treating osteopenic conditions are described. Methods and compounds for increasing bone mineral density by decreasing serotonin levels in osteoblasts are also described.

5 Claims, 10 Drawing Sheets

FIG. 1    Analysis of Tibiae by microCT
K/O and WT animals
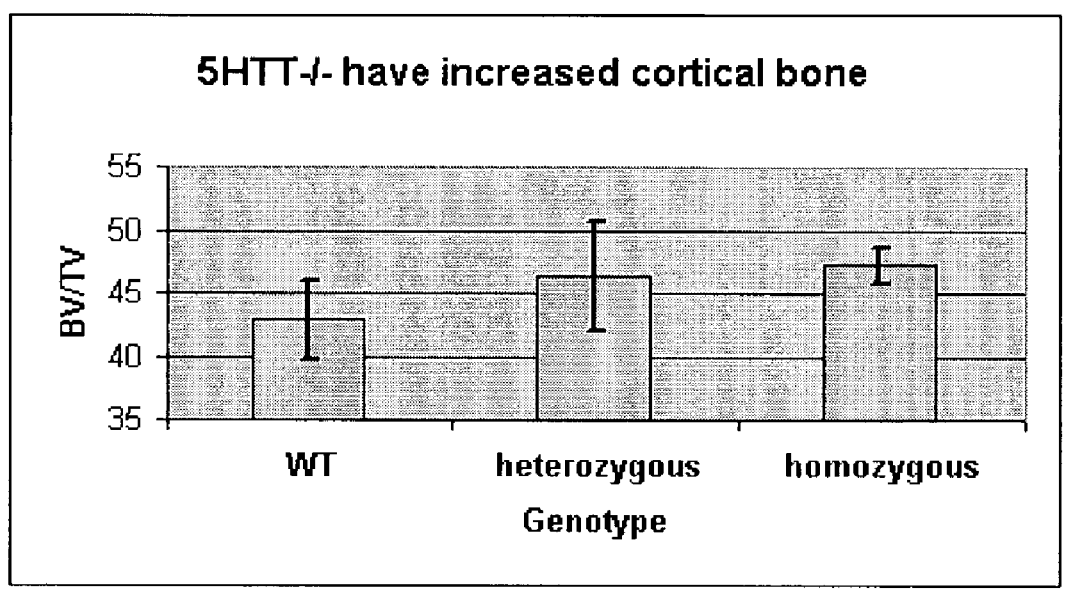

Systemic Fluoxetine increases trabecular parameters

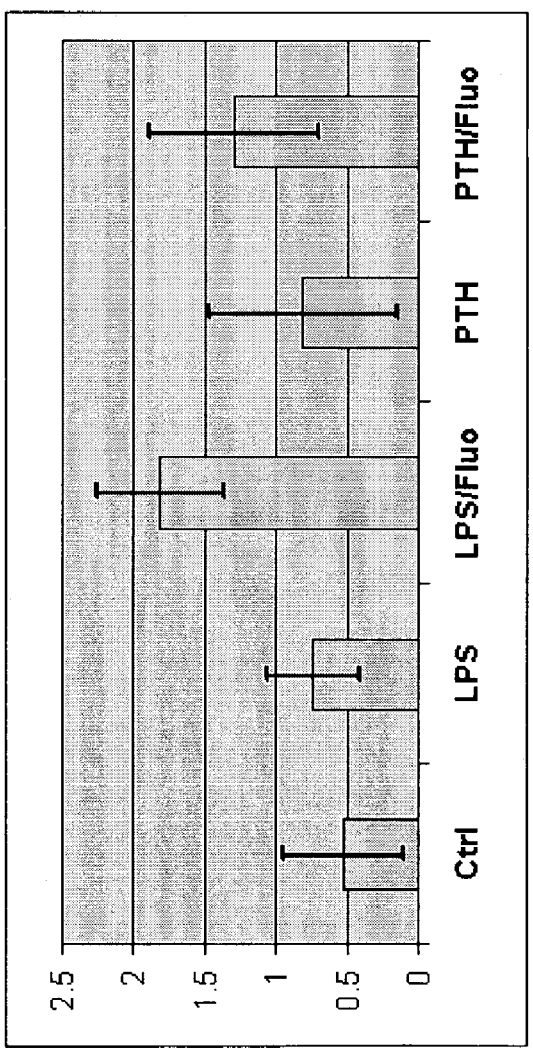
FIG. 3: Systemic Fluoxetine also results in new bone. LPS and PTH were injected over the mouse calvarium with/without fluoxetine FIG. 4   Subcutaneous injections of LPS results in increased new bone formation in 5HTT -/- (LPS-4) compared to wt mice (LPS-2)
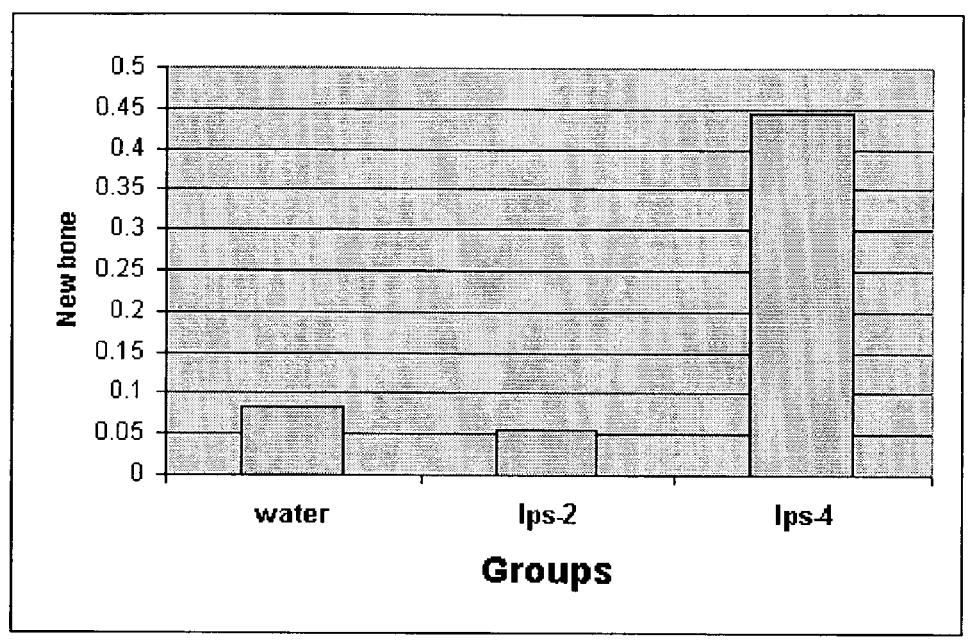

FIG. 5    Fluoxetine increases bone nodule formation *in vitro*
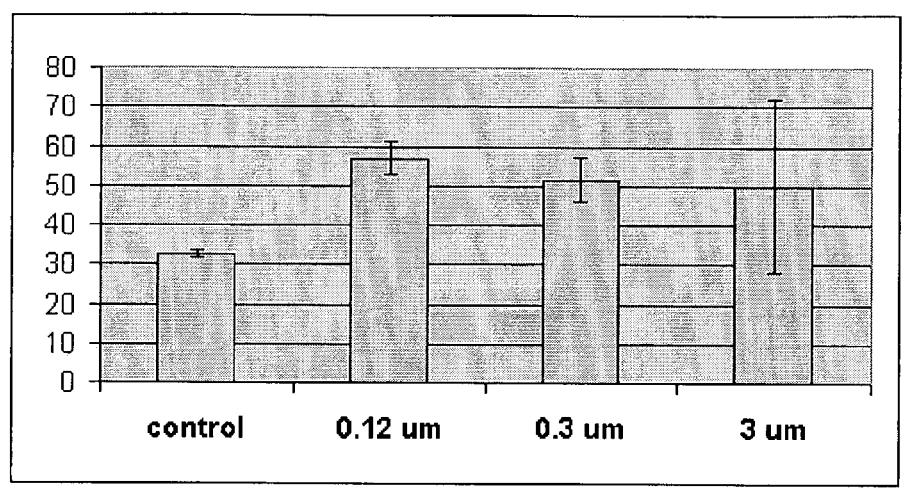
Mouse primary osteoblasts were cultured *in vitro* with different concentrations of Fluoxetine bone nodules were stained with Von Kossa and counted

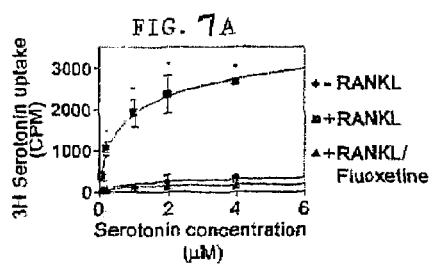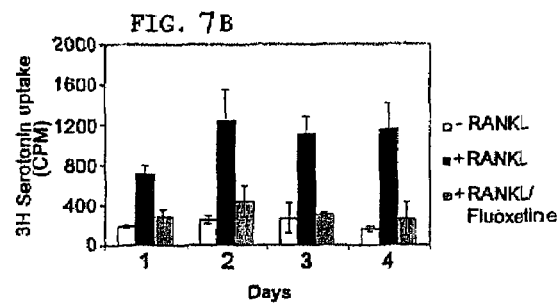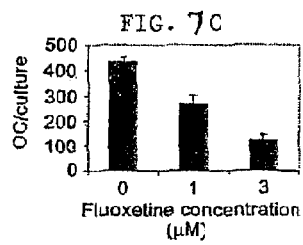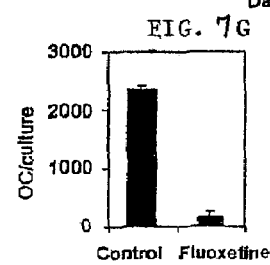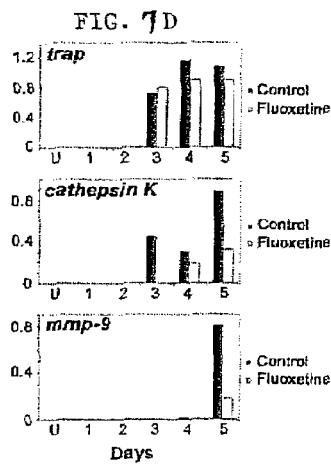

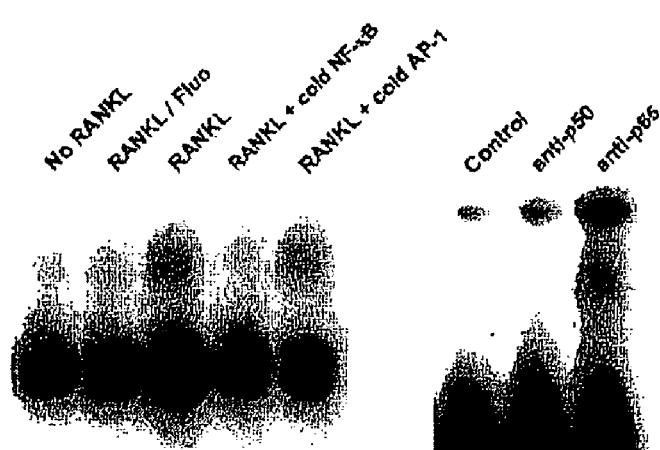
FIG. 9A
FIG. 9B
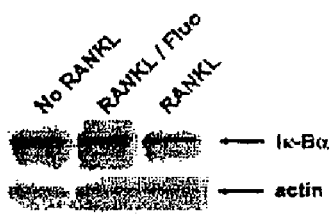
FIG. 9C

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
                        oligonucleotide primer

<400> SEQUENCE: 1
gaccagtgtg gtgaactgca tgac                                          24

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:
                        oligonucleotide primer

<400> SEQUENCE: 2
gatgatggca aagaatgtgg atgctg                                        26

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
                        oligonucleotide primer

<400> SEQUENCE: 3
acgtttgcag gcctggaagg                                               20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
                        oligonucleotide primer
```

```
<400> SEQUENCE: 4
acacagcatt catgcggatg tcc                                          23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
gaagagctat gagctgcctg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6
cacagagtac ttgcgctcag                                              20

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 7
acacagtgat gctgtgtggc aactc                                        25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
ccagaggctt ccacatatat gatgg                                        25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
ctgaagatgc tttcccatat gtggg                                        25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer
```

-continued

```
<400> SEQUENCE: 10
gcaggcgttg ttcttattcc gagc                                        24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
tccaggctga ggagtggtac tttgg                                       25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 12
atacggtagt gaggcggtga cacag                                       25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 13
cgagtggacg cgaccgtagt tgg                                         23

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 14
caggcttaga gccacgacca tacag                                       25

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15
agttgagggg atttcccagg c                                           21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer
```

```
<400> SEQUENCE: 16
tcaactcccc tgaaagggtc cg                                              22
```

METHODS FOR INCREASING BONE DENSITY

RELATED APPLICATIONS

This application claims the benefit of U.S. Provisional Application No. 60/385,314, filed May 31, 2002, the entire contents of which is hereby incorporated by reference.

GOVERNMENT SUPPORT

The invention was supported, in whole or in part, by grant DE-07378 from the National Institutes of Health. The Government has certain rights in the invention.

BACKGROUND OF THE INVENTION

Bone production by osteoblasts and resorption by osteoclasts is critical for normal bone development and remodeling. Excessive resorption is a key pathogenic component in osteopenic conditions such as osteoporosis, arthritis, periodontitis and certain malignancies. Bone resorption is regulated by a complex system of hormones and locally-produced cytokines that stimulate osteoblasts and stromal cells to express Receptor Activator of NF-κB Ligand (RANKL), resulting in the differentiation and activation of osteoclasts. The processes by which osteoclast differentiation and activation occur are currently not well understood.

Regulators of osteoclastic resorption and bone production by osteoblasts are currently not well understood.

SUMMARY OF THE INVENTION

The invention is based on the discovery that a class of compounds known as serotonin reuptake inhibitors activates osteoblast cells. Accordingly, the invention provides methods of stimulating bone formation by contacting an osteoblast with an osteoblast-stimulatory amount of a serotonin reuptake inhibitor (i.e. an inhibitor of serotonin transport). The serotonin reuptake inhibitor is a selective serotonin reuptake inhibitor or a non-selective serotonin reuptake inhibitor. The inhibitor binds to a serotonin transport molecule, such as, 5-hydroxytryptamine transporter (5-HTT). This binding reduces the transport of serotonin into the cell. The methods are useful for regulating bone formation, bone resorption, and bone mineral density.

An osteoblast-stimulatory amount is an amount that activates an osteoblast. Osteoblast activation is measured or determined by the deposition of bone mineral, for example by quantitating bone nodule formation in vitro or by bone densitometry in vivo. Osteoblast activation is also measured by expression of biochemical markers associated with bone formation. Biochemical markers of bone formation include serum bone-specific alkaline phosphatase, serum osteocalcin, and serum propeptide of type I procollagen.

Selective serotonin reuptake inhibitors (SSRIs) include fluoxetine, citalopram, paroxetine, sertraline, fluvoxamine, escitalopram, and salts thereof. Non-selective serotonin reuptake inhibitors include heterocyclic compounds. Examples of heterocyclic compounds that primarily inhibit serotonin reuptake include: clomipramine, amitriptyline, imipramine, and salts thereof. In addition, trazodone is a serotonin antagonist and serotonin reuptake inhibitor, and venlafaxine is a non-cyclic, serotonin-norepinephrine reuptake inhibitor (SNRI).

Inhibitors of serotonin transport include a compound of Formula I, or a pharmaceutically acceptable salt (e.g., an acid addition salt of a pharmaceutically acceptable acid) thereof:

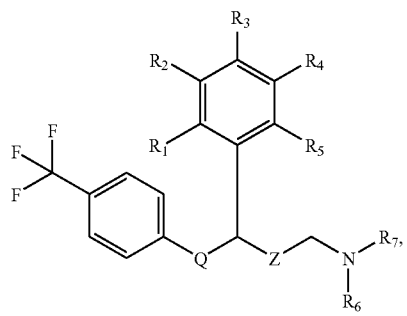

I where Q is O, S, or N;
Z is a $C_1$-$C_6$ straight or branched alkyl;
$R_1$-$R_5$ are, independently, hydrogen, amino, or substituted or unsubstituted $C_1$-$C_6$ alkyl, where the substituents are halo, hydroxy, alkoxy, carboxy, or amino;
$R_6$ and $R_7$ are, independently, hydrogen or a $C_1$-$C_6$ straight or branched alkyl.

In some embodiments, the compound is a compound of Formula II, or a pharmaceutically acceptable salt thereof:

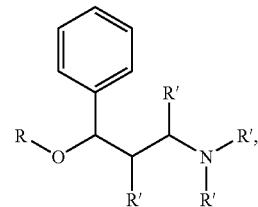

II where each R' is hydrogen or methyl, R is naphthyl or:

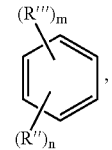

where R" and R'" are halo, trifluoromethyl, $C_1$-$C_4$ alkyl, $C_1$-$C_3$ alkoxy, or $C_3$-$C_4$ alkenyl, where m and n are 0, 1, or 2.

In formula II, when R is naphthyl, it can be either α-naphthyl or β-naphthyl. R" and R'" when they are halo, $C_1$-$C_4$ alkyl, $C_1$-$C_3$ alkyloxy or $C_3$-$C_4$ alkenyl represent, illustratively, the following atoms or groups: fluoro, chloro, bromo, iodo, methyl, ethyl, isopropyl, n-propyl, n-butyl, isobutyl, sec.-butyl, t-butyl, methoxy, ethoxy, n-propoxy, isopropoxy, allyl, methallyl, crotyl and the like. R thus can represent o, m and p-trifluoromethylphenyl, o, m and p-chlorophenyl, o, m and p-bromophenyl, o, m and p-fluorophenyl, o, m and p-tolyl, xylyl including all position isomers, o, m and p-anisyl, o, m and p-allylphenyl, o, m and p-methylallylphenyl, o, m and p-phenetolyl(ethoxyphenyl), 2,4-dichlorophenyl, 3,5-difluorophenyl, 2-methoxy-4-chlorophenyl, 2-methyl-4-chlorophenyl, 2-ethyl-4-bromophenyl, 2,4,6-trimethylphenyl, 2-fluoro-4-trifluoromethylphenyl, 2,4,6-trichlorophenyl, 2,4,5-trichlorophenyl, and the like. See, e.g., U.S. Pat. No. 4,314,081; U.S. Pat. No. 4,626,549.

A representative compound is fluoxetine hydrochloride ((+/−)—N-methyl-3-phenyl-3-[(α,α,α-trifluoro-p-tolyl)oxy]propylamine hydrochloride; Prozac):

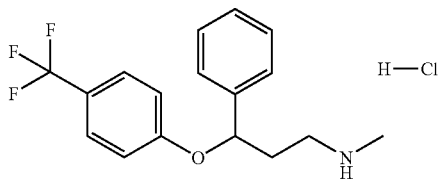

Also within the invention is a method of stimulating bone formation by identifying a subject that is suffering from or is at risk of developing an osteopenic condition, and contacting an osteoblast of the subject with a serotonin reuptake inhibitor. Bone formation is increased in the presence of the inhibitor compared to in its absence. The methods are useful for alleviating a symptom of or treating an osteopenic condition. Subjects suffering from or at risk of developing an osteopenic condition have a bone mass density value that is at least one standard deviation below a reference bone mass density value of an age-matched individual or index. For example, the index is an average of values obtained from a normal age-matched population of subjects. Preferably, the subject has not been diagnosed with depression, a depressive disorder, or an anxiety-related disorder.

An osteopenic condition is a condition in which bone mineral density is decreased compared to a normal control value. Bone mineral density is assigned a T-score, which is a relative term describing the number of standard deviations from the value at peak bone density. The World Health Organization has defined osteoporosis and osteopenia based on these values. The T-score is the number of standard deviations from the mean (average) value. Normal bone is defined as bone with a T-score better than −1 (i.e. ≦1 standard deviation less than the mean). Osteopenia is defined as a T-score between −1 and −2.5 (i.e. 1-2.5 standard deviations less than the mean), and osteoporosis is defined as a T-score of less than −2.5 (i.e. ≧2.5 standard deviations less than the mean).

An osteopenic condition or the risk of developing an osteopenic condition is diagnosed by measuring bone density. Several methods are available to measure bone density including, x-ray, dual energy x-ray absorptiometry (DEXA), single energy x-ray absorptiometry (SXA), ultrasound, quantitative computed tomography (QCT), and magnetic resonance.

Osteopenic conditions occur in trabecular bone and in cortical bone. The methods of the invention can be used to increase the bone mass of cortical bone or trabecular bone. The compounds described herein are administered systemically or locally, e.g. deposited adjacent to a target bone or directly into a target bone.

Cortical bone serves as a protective covering and surrounds trabecular bone. The ratio of cortical and trabecular bone combination varies throughout the bones of the body. Cortical bone is predominant in the limbs (the Appendicular skeleton), and is responsible for the skeleton's strength. Cortical bone may be referred to as Haversian or compact bone. Cortical bone mainly consists of: collagen protein and hydroxyappatite (calcium phosphate salts).

The bones of the axial skeleton, which include the rib cage, the backbone and the skull, have a higher proportion of trabecular bone than the bones in the appendicular skeleton. Trabecular bone is also known as spongy or cancellous bone. At the ends of long bones i.e., the femur in the leg or the radius in the arm, the cortical bone becomes thinner and the bone is predominantly made up of trabecular bone. This predominance of trabecular bone compared to cortical bone is also found in the vertebrae.

The invention also includes methods of identifying compounds which increase bone formation. An osteoblast is contacted with a candidate compound and serotonin transport is measured. A decrease in serotonin transport in the presence of a compound compared to serotonin transport in the absence of the compound indicates that the compound increases bone formation.

Serotonin transport is assayed directly by radiolabelling serotonin with tritium and measuring the amount of radioactive serotonin in the cell. Serotonin transport is also assayed indirectly by measuring the amount of radiolabelled serotonin remaining in the serum. The amount of serotonin is optionally measured in the presence or absence of competitive inhibitors of serotonin uptake. Alternatively, intracellular or extracellular serotonin is quantitated using anti-serotonin antibodies in conjunction with assays such as ELISA and densitometric techniques known in the art.

Other features and advantages of the invention will be apparent from the following detailed description and from the claims.

BRIEF DESCRIPTION OF THE DRAWINGS

FIG. 1 is a bar graph comparing bone volume per total volume (BV/TV) in wildtype mice and mice lacking 5-HTT (5-hydroxytryptamine transporter i.e., serotonin transporter).

FIG. 3 is a bar graph showing that systemic administration of fluoxetine results in new bone formation. Co-administration of fluoxetine and lipopolysaccharide (LPS) or fluoxetine and parathyroid hormone (PTH) showed a greater increase in new bone than with the administration of LPS or PTH alone.

FIG. 4 is a bar graph showing that subcutaneous injection of LPS results in significant increase in new bone formation in mice lacking the serotonin transporter (5-HTT −/−) compared to LPS-injected wildtype mice.

FIG. 5 is a bar graph showing increased bone nodule formation by osteoblasts incubated with fluoxetine in vitro.

Figures 6A, 6B:
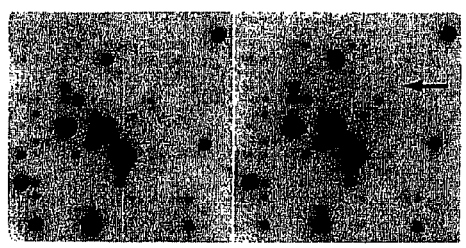
FIG. 6A is a scanned image of a gene array hybridized to mixed cDNA probes from undifferentiated RAW 264.7 cells.
FIG. 6B is a scanned image of a gene array hybridized to mixed cDNA probes from RANKL-induced RAW 264.7 cells. Up-regulation of the 5-hydroxytryptamine transporter (5-HTT) is indicated by the arrow.
Figure 6C:
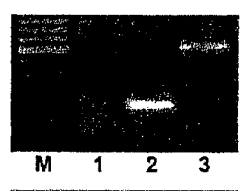

FIG. 6C is a photograph of an electrophoretic gel showing the results of reverse transcriptase-polymerase chain reaction products indicating 5-HTT expression levels in RAW 264.7 cells. (M: standard; lane 1: 5-HTT expression in cells having no RANKL induction; lane 2: 5-HTT expression in cells having 4 days of RANKL induction; lane 3: β-actin expression in cells having 4 days of RANKL induction)

Figure 6D:
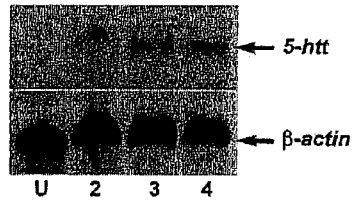

FIG. 6D is a photograph of an electrophoretic gel showing the results of a Northern blot analysis of 5-HTT and β-actin expression in RAW 264.7 cells. (U: no RANKL stimulation; lanes 2-4: cells stimulated with RANKL for 2, 3, and 4 days, respectively)

Figure 6E:

FIG. 6E is a photograph of stained cells showing 5-HTT expression in multinucleated osteoclasts (control antibody).

Figure 6F:

FIG. 6F is a photograph of stained cells showing 5-HTT expression in multinucleated osteoclasts (anti-5-HTT antibody).

FIG. 7A is a line graph of the effect of fluoxetine on the uptake of 5-hydroxytryptamine (5-HT) by the osteoclast-expressed transporter. RAW 264.7 cells were cultured in the presence (+RANKL) or absence (−RANKL) of RANKL. The uptake of $^3$H-labeled 5-HT was assessed in the presence (+RANKL/fluoxetine) or absence (+RANKL) of fluoxetine. $*p<0.01$).

Figure 2A:
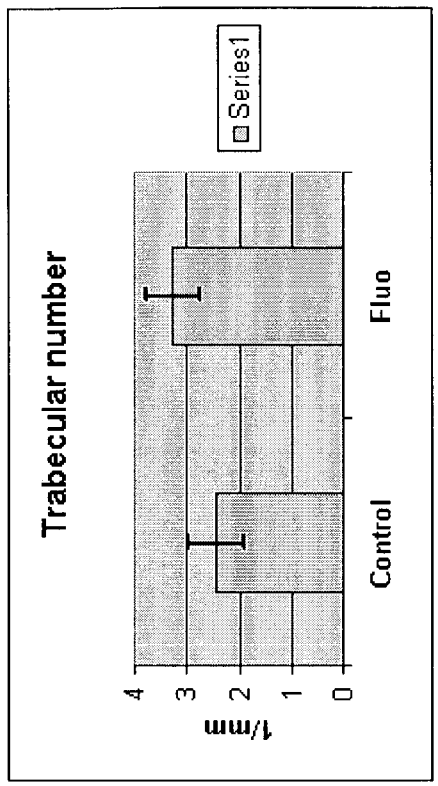
FIG. 2A is a bar graph showing decreased trabecular spacing after treatment with fluoxetine compared to no treatment.

FIG. 7B is a bar graph showing the kinetics of acquisition of 5-HTT activity in the RAW 264.7-derived osteoclasts described in FIG. 2A over time (days).

FIG. 7C is a bar graph showing the effect of fluoxetine concentration on RANKL-induced osteoclast formation by RAW 264.7 cells. Osteoclasts were quantified by multinuclearity and tartrate-resistant acid phosphatase (TRAP) staining. $*p<0.01$.

FIG. 7D is a bar graph showing the effect of fluoxetine (3 mM) on the expression of the osteoclastic TRAP gene in RANKL-stimulated RAW 264.7 cells (dark bars) or unstimulated cells (white bars). (U: untreated cells; 1-5: days of RANKL stimulation)

FIG. 7E is a bar graph showing the effect of fluoxetine (3 mM) on the expression of the osteoclastic cathepsin K gene in RANKL-stimulated RAW 264.7 cells (dark bars) or unstimulated cells (white bars). (U: untreated cells; 1-5: days of RANKL stimulation)

FIG. 7F is a bar graph showing the effect of fluoxetine (3 mM) on the expression of the osteoclastic matrix metalloprotease-9 (MMP-9) gene in RANKL-stimulated RAW 264.7 cells (dark bars) or unstimulated cells (white bars). (U: untreated cells; 1-5: days of RANKL stimulation)

FIG. 7G is a bar graph showing the effect of fluoxetine on RANKL-induced osteoclast formation by normal bone marrow macrophages (BMM). BMM were cultured in the presence of macrophage-colony stimulating factor (M-CSF) and RANKL, and the number of osteoclasts were quantified by TRAP staining. $*p<0.001$. (Control: no cell treatment)

Figure 8A:
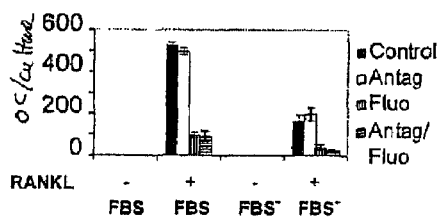

FIG. 8A is a bar graph showing the effect of serum depleted of 5-HT (FBS) or replete with 5-HT (FBS), which were left untreated (Control), exposed to fluoxetine (Fluo), exposed to a mixture of receptor antagonists specific for 5-HT1B, 5-HT2B, and 5-HT4, or exposed to fluoxetine plus the mixture of antagonists (Antag/Fluo) on the differentiation of RANKL-induced (+) or uninduced (−) RAW 264.7 cells (assessed by measuring TRAP positive multinucleated cells); $*p<0.01$ FIG. 8B is a bar graph showing the effect of 5-HT (0 ng/ml, 3 ng/ml, 30 ng/ml, or 300 ng/ml) administered to RAW 264.7 cells in 5-HT-depleted FBS (FBS) on cathepsin K expression at Days 3 and 4 after RANKL induction, as measured by Northern blot analysis and quantitation of band intensity (standardized to the expression of GAPDH).

Figure 8C:
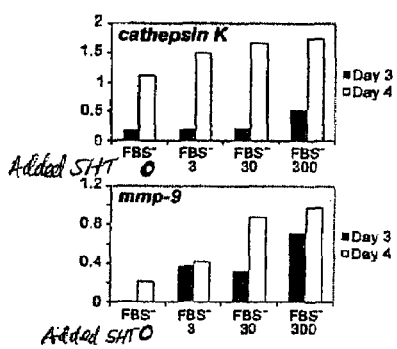

FIG. 8C is a bar graph showing the effect of 5-HT (0 ng/ml, 3 ng/ml, 30 ng/ml, or 300 ng/ml) administered to RAW 264.7 cells in 5-HT-depleted FBS (FBS) on MMP-9 expression at Days 3 and 4 after RANKL induction, as measured by Northern blot analysis and quantitation of band intensity (standardized to the expression of GAPDH).

Figure 8E:
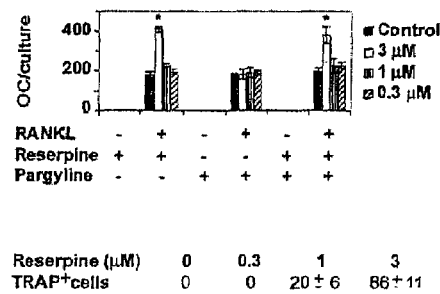
Figure 8D:
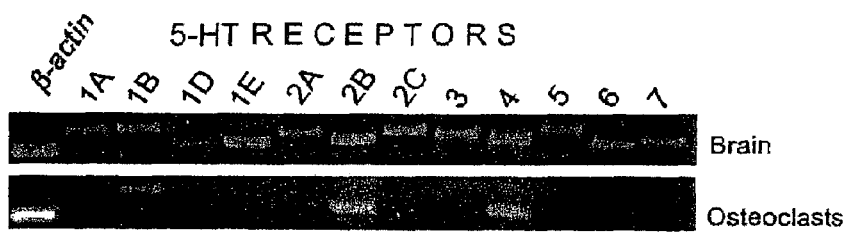

FIG. 8D is a photograph of an electrophoretic gel showing β-actin and 5-HT receptors 1A, 1B, 1D, 1E, 2A, 2B, 2C, 3, 4, 5, 6, and 7 reverse transcriptase-polymerase chain reaction products in brain and in RANKL-induced osteoclasts after 4 days in culture.

FIG. 8E is a bar graph showing the effect of the vesicular monoamine transporter (VMAT) inhibitor reserpine, or the monoamine oxidase-B (MAO-B) inhibitor pargylline, alone or in combination, on osteoclast formation in RAW 264.7 cells induced with RANKL or left uninduced, in the presence of no 5-HT, 0.3 μM 5-HT, 1 μM 5-HT, or 3 μM 5-HT as assessed by quantitation of TRAP+ multinucleated osteoclasts. $*p<0.05$.

FIG. 8F is a table of the effect of various concentrations of reserpine (0 μM, 0.3 μM, 1 μM, or 3 μM) on the number of mono- and bi-nucleated RAW 264.7 cells expressing TRAP.

FIG. 9A is a photograph of an electrophoretic gel showing the results of an electrophoretic mobility shift assay showing that NF-κB activity is not upregulated in unstimulated RAW 264.7 cells (No RANKL), is upregulated in RANKL-stimulated RAW 264.7 cells (RANKL), is inhibited by fluoxetine in RANKL stimulated cells (RANKL/Fluo), and is blocked by 100-fold excess cold NF-κB oligodeoxynucleotide (ODN) (RANKL+cold NF-κB), but not by cold AP-1 ODN (RANKL+cold AP-1).

FIG. 9B is a photograph of an electrophoretic gel showing the results of an electrophoretic mobility super shift assay showing retardation of the NF-κB binding complex by anti-p65 (anti p-65), but not by anti-p50 (anti p-50) or a non-specific antibody control (Control)).

FIG. 9C is an autoradiograph of a Western blot showing Iκ-Bα and actin expression in unstimulated cells (No RANKL), RANKL-induced osteoclasts (RANKL), and RANKL induced osteoclasts also treated with fluoxetine (RANKL/Fluo).

Figure 10B:
Figure 10A:
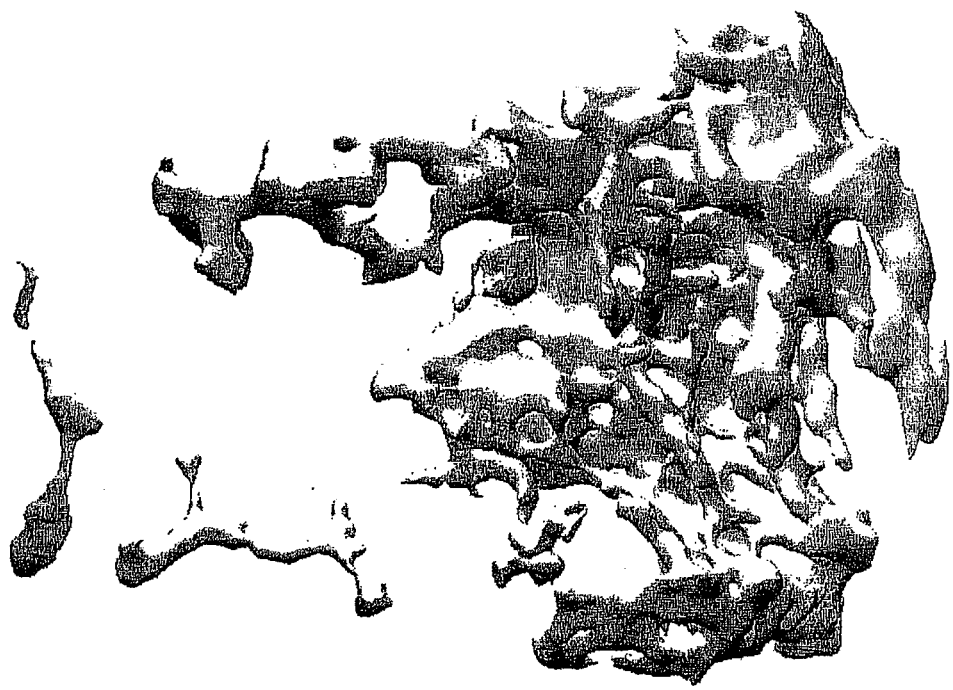

FIG. 10A is a photograph of trabecular bone in fluoxetine-treated mice.

FIG. 10B is a photograph of trabecular bone in untreated mice.

DETAILED DESCRIPTION OF THE INVENTION

Osteopenia refers to a condition characterized by lower than normal bone density, and osteoporosis is a more advanced stage of the condition. Bone density naturally declines with age or may develop as an adverse side effect of a medication. Current treatment recommendations include estrogen (for women), calcium, exercise. However, there are risks (e.g., cancer) associated with hormone replacement therapy for women. Other drugs such as alendronate and calcitonin are used to treat the condition; however, the long-term safety of these drugs is unknown. The invention is based on the discovery of a previously unknown activity of serotonin reuptake inhibitor compounds. Methods of stimulating bone formation are carried out by administering systemically (or locally at or near a target bone site) an osteoblast-stimulatory amount of an inhibitor of serotonin transport. This class of compounds have been in clinical use for many years and have been shown to be safe for long-term use. The inhibitors decrease the level of serotonin transport in a cell, e.g., by binding to a serotonin transport molecule, such as, 5-hydroxytryptamine transporter (5-HTT).

Serotonin 5-hydroxytryptamine (5-HT, i.e. serotonin) has been known for a half century to participate in neurotransmission, nociception, and vasoactivity. Extracellular levels of 5-HT are regulated by uptake by the 5-hydroxytryptamine transporter (5-HTT), thus limiting its action on receptors. However, growing evidence indicates a broader role for the 5-HTT and for the serotonergic system in general, in the development and regulation of both neural and non-neural tissues. 5-HTT mRNA is widely expressed prior to organogenesis and throughout the second half of gestation, particularly in developing sensory ganglionic neurons and neuroepithelial cells, in neural crest and neural crest-derived tissues, and in the craniofacial and cardiac regions, suggesting a role in regulation of peripheral synaptogenesis. Embryos exposed to SSRIs and receptor ligands exhibit craniofacial malformations, possibly via effects on epithelial-mesenchymal interactions. The data described herein provide evidence for an additional role of the 5-HT system, in the regulation of osteoclasts and osteoblasts, and in bone modeling and remodeling.

5-HT has been detected in the nucleus as well as the cytoplasm of various cells during embryogenesis, suggesting novel pathways of intracellular transport, as well as possible direct modulatory effects of 5-HT on signaling or gene transcription. In addition, it has recently been found that 5-HT receptors may be expressed both on the neuronal cell surface, as well as in the cytoplasm, where they may associate with smooth endoplasmic reticulum-like organelles.

There are a number of sources of 5-HT in vivo. Although modest levels are present in the circulation, 5-HT is released in locally high concentrations from sensory nerve plexuses, paraneurons, platelets, and mast cells. Mast cells are present in bone marrow, and their numbers increase dramatically in ovariectomized rats which suffer rapid bone loss. The human disorder mastocytosis is also significantly associated with osteoporosis.

Genes Related to SSRI Action

The SSRIs appear to share similar pharmacodynamic properties, which translate to major depressive disorders MDD-treatment efficacy. The primary mode of SSRI action is binding to the serotonin transporter (5-HTT), inhibiting its capacity to transport serotonin and, thus, raising the synaptic serotonin level, with consequently increased stimulation of one or more types of serotonergic (5-HT) receptor. The 5-HTT transgenic knockout mouse is an art-recognized model of serotonin reuptake inhibition.

Serotonin Transporter

Functional polymorphisms in the 5-HTT gene (5-HTTLPR, VNTR) have been associated with personality traits, hyper kinetic disorders, schizophrenia and unipolar depression, and clinical response to SSRIs. Clinically, the use of SSRIs for the treatment of depression and other psychological disturbances is widespread and is increasing.

It has been determined that, in terms of transcriptional activity, the long (l) variant in the 5-HTT gene-linked polymorphic region (5-HTTLPR) is more than twice as active as the short (s) analog. Thus, most of the recent pharmacogenetic SSRIs studies have focused on the 5-HT-TLPR polymorphism. An association between therapeutic fluvoxamine response and the 5-HTTLPR polymorphism has been demonstrated, with better response to fluvoxamine demonstrated for the l-allele carriers (l/l and l/s) in comparison to s-variant (s/s) homozygotes.

An evaluation of the links between 5-HTT polymorphisms, the use of anti-depressants, and effects on skeletal homeostasis is therefore timely and advantageous.

The results described herein demonstrate serotoninergic regulation of osteoclast and osteoblast development and/or activation. The 5-HT and 5-HT receptors are expressed on osteoblasts as well as osteoclasts. These cells interact to regulate bone mass therefore, the net effect of the serotonergic system on bone mass is likely to be complex in vivo.

Osteopenic Conditions

The T-score is used as an indicator for risk of osteopenic conditions, and in the diagnosis of osteopenic conditions. Table 1 shows the average bone mass density values for Caucasian woman or man in standardized values at the hip. The same cut-off values for the T-scores were used for men as for women, although not all studies show that the fracture risk is the same for men and women with identical bone density values (in g/cm2).

TABLE 1

|     | Average Woman | | Average Man | |
| --- | --- | --- | --- | --- |
| Age | mg/cm2 | T-score | mg/cm2 | T-score |
| 25 | 955 | zero | 1055 | +0.81 |
| 35 | 945 | −0.08 | 1038 | +0.67 |
| 45 | 920 | −0.28 | 1002 | +0.38 |
| 55 | 876 | −0.64 | 990 | +0.28 |
| 65 | 809 | −1.19 | 969 | +0.11 |
| 75 | 740 | −1.75 | 928 | −0.21 |
| 85 | 679 | −2.24 | 859 | −0.78 |

These numbers are the standardized values from a stratified representative sample (N=14,646) of the noninstitutionalized population of the U.S. (see e.g., Looker, A. C., *Osteoporos Int* 8: 468-89 (1998)). The standard deviation for young women is 123. Values for Mexican Americans are very similar to those for whites, but black men and women have much higher values.

The World Health Organization has defined osteoporosis and osteopenia based on these values. T-score is the number of standard deviations from the mean (average) value. Normal bone is defined as bone with a T-score better than −1 (i.e. ≦1 standard deviation less than the mean). Osteopenia is defined as a T-score between −1 and −2.5 (i.e. 1-2.5 standard deviations less than the mean), and osteoporosis is defined as a T-score of less than −2.5 (i.e. ≧2.5 standard deviations less than the mean). Clinically established osteoporosis includes the presence of a non-traumatic fracture.

Other risk factors associated with osteopenic conditions and osteoporosis are listed in Table 2.

TABLE 2

| Genetic Factors |
| --- |
| White or Asian ethnicity |
| Positive family history osteoporosis, osteopenia, Marfan's disease |

TABLE 2-continued

Small body frame (less than 58 kg)
Female

Lifestyle/History Factors

Smoking
Inactivity
Nulliparity
Excessive exercise (producing amenorrhoea)
Females never having had Hormone Replacement Therapy
History of Bone Fractures
Early natural menopause or Bilateral Ovariectomy
Late menarche Nutritional Factors Milk intolerance
Low dietary calcium intake
Excessive alcohol intake
Consistently high animal protein intake Medical Disorders Anorexia nervosa
Thyrotoxicosis
Cushing's syndrome
Type I diabetes
Alterations in gastrointestinal and hepatobiliary function
Occult osteogenesis imperfecta
Mastocytosis
Rheumatoid arthritis
Long-term parenteral nutrition
Prolactinoma
Haemolytic anaemia, haemochromatosis, and thalassaemia
Ankylosing spondylitis Drugs Thyroid replacement drugs
Glucocorticoid drugs
Anticoagulants (heparin)
Chronic lithium therapy
Chemotherapy
Gonadotropin Releasing Hormone agonist or antagonist therapy
Anticonvulsant drugs
Extended tetracycline use
Diuretics producing calciuria
Phenothiazine derivatives
Cyclosporin
Aluminium-containing antacids The risk factors for and the methods of diagnosing osteoporosis and osteopenic conditions differ from the risk factors for and the methods of diagnosing depression, depressive disorders, and anxiety-related disorders.

Examples of osteopenic conditions, include arthritis (e.g., rheumatoid arthritis, juvenile arthritis, osteoarthritis, juvenile rheumatoid arthritis, Lyme arthritis, and psoriatic arthritis), osteoporosis, periodontitis, Paget's disease, Cushing's syndrome, and cancers, e.g., myeloma.

Certain cancers, for example, multiple myeloma, lymphoma, leukemia, and gastrointestinal carcinomatosis can result in diffuse loss of bone, especially the trabecular bone of the vertebral column, even in the absence of hypercalcemia.

Paget's disease is characterized by radiologic features similar to osteoporosis. In addition, other indicators for Paget's disease include high alkaline phosphatase levels and moderately or markedly increased urinary excretion of hydroxyproline-containing peptides.

Cushing's syndrome is associated with development of osteoporosis. Elevated blood levels of cortisol are an indicator of Cushing's syndrome.

Parathyroid hormone (PTH), 1,25-dihydroxyvitamin D, and calcitonin are involved in controlling calcium homeostasis. Hyperparathyroidism is characterized, in part, by increased levels of PTH. Increased concentration of PTH has been shown to stimulate bone remodelling by increasing the activation of "remodelling units". A remodelling unit is the entire group of cells involved in removing and replacing a packet of bone—osteoclasts, reversal cells, and osteoblasts.

Some malignancies have been associated with the production of parathyroid hormone related protein (PTHrp). Increased levels of PTHrp have been shown to stimulate bone remodelling.

Osteopenic conditions can be characterized by abnormal levels of PTH, calcium, phosphorus, and vitamin D in the blood or urine. Vitamin D metabolism is regulated by the kidneys. Conditions of renal failure are associated with osteopenia. Loss of kidney function can be correlated with increased blood creatinine.

Lipopolysaccharide (LPS) is involved in mediating bacterially induced bone destruction, such as occurs in osteomyelitis, bacterial arthritis, and periodontal diseases. LPS has been reported to potently stimulate bone resorption in both in vitro and in vivo studies. LPS has been reported to induce osteoclast formation in bone marrow culture, and local injection of LPS into the femur was found to lead to a rapid increase in the number of osteoclasts.

Osteoporotic fractures mainly affect the spine (vertebral crush fractures), leading to loss of height, kyphosis, and chronic back pain; the distal radius (Colles' fracture); and the most clinically significant, the proximal femur ("hip fractures").

Methods of Treating Osteopenic Conditions

The terms "therapeutic" and "treatment" as used herein, refer to ameliorating one or more symptoms associated with a disease or condition, including preventing or delaying the onset of the disease symptoms, and/or lessening the severity or frequency of symptoms of the disease. The term "subject" or "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species.

The invention provides a method of treating an osteopenic condition in a subject in need of such treatment by decreasing serotonin levels and/or activity in the osteoblasts of the subject. Serotonin levels and/or activity are decreased in the osteoblasts of the subject by administering to the subject an inhibitor of serotonin transport or a derivative thereof.

Methods of Bone Remodeling and Increasing Bone Mineral Density

Bone remodeling is carried out by osteoclasts (resorb bone), by "mononucleated reversal cells" (prepare lacunar surfaces for new bone formation and/or recruit or summon osteoblast precursors), and by osteoblasts (generate new bone). It is the activities of a combination of these cell types that regulates overall bone remodeling.

Compounds that decrease serotonin levels in osteoblasts induce or increase osteoblast activation, leading to increased bone production. The treatment of mice with an inhibitor of serotonin transport, such as a selective serotonin reuptake inhibitor increases bone mass density in mice.

Selective serotonin reuptake inhibitors (SSRIs) are naturally-occurring or artificially-derived compound that inhibit (decrease or prevent) the uptake of serotonin by cells, for example, neuronal cells, osteoclasts, or osteoblasts. Such inhibition can occur by an agent that binds to either serotonin or the serotonin transporter, such that interaction between serotonin and the serotonin transporter is inhibited.

Examples of SSRIs include: fluoxetine, citalopram, paroxetine, sertraline, fluvoxamine, escitalopram, and derivatives or mimeotopes thereof.

Derivatives are compounds that can be formed from an existing (reference) compound by replacement of one or more atoms or functional groups with another atom, group of atoms, or functional groups. Preferably, the derivative functions in a manner that is similar to the reference compound, and has an increased or decreased level of activity, or is less toxic, or more immunologically tolerable than the reference compound.

Mimeotopes are compounds that mimic the functional activity of a reference compound. Mimeotopes can be structurally similar or disimilar to the reference compound. Mimeotopes are compounds that work via the same biochemical mechanism as the reference compound. For example, a mimeotope of fluoxetine decreases serotonin transport.

Serotonin levels and/or activity can also be decreased in the osteoblasts of a subject by increasing vesicular monoamine transporter expression and/or activity in the osteoblasts. A vesicular monoamine transporter (VMAT) is a polypeptide that mediates the uptake of monoamines in cells. Examples of monoamines normally taken up by VMATs include serotonin, catacholamines, indolamines, and dopamine. The amino acid and nucleotide sequences of human VMAT polypeptides are available from the GenBank database (at ncbi.nlm.nih.gov as available on May 30, 2002). VMAT expression and/or activity in cells can be increased in a number of ways, for example, by administering an agent that increases the activity and/or expression of a VMAT, or by overexpressing VMAT.

Serotonin levels and/or activity are decreased in the osteoblasts of a subject by administering to the subject an inhibitor of serotonin function (activity) or a derivative thereof. Inhibitors of serotonin function are agents that decrease or prevent one or more of the activities of serotonin. Inhibitors of serotonin function include, for example, agents that bind to serotonin itself, and agents that bind to molecules involved in uptake of serotonin by cells, as well as agents that regulate production of serotonin in the cell, thereby resulting in decreased intracellular levels of serotonin and concomitant decreased levels of serotonin function. Inhibitors of serotonin function include SSRIs, agents that increase VMAT activity and/or expression, small organic molecules, such as substrate and/or cofactor analogs or mimics (e.g., transition state analogs), active-site labeling agents, serotonin reaction product mimics, antibodies, polymorphic serotonin transporters that alter the function of the transporter, dominant negative polypeptides, peptidomimetics, and mutants of a natural serotonin substrate.

The inhibitors can be a competitive inhibitor, or a non-competitive inhibitor. Inhibitors of serotonin function can be identified, for example, by measuring uptake of serotonin by cells in the presence of the inhibitor, or by measuring osteoblast differentiation or activity in the presence of the agent. Measures of osteoblast differentiation or activation include measuring the synthesis of collagen type I, the expression of alkaline phosphatase activity, the expression of osteocalcin, intracellular cAMP stimulation by parathyroid hormone and the ability to mineralize the extracellular matrix, and the expression of osteonectin, osteopontin, and vitamin D receptors. Preferably, the inhibitor inhibits serotonin function by at least about 10%, 25%, 50%, 60%, 70%, 80% 90% or 100% compared to a suitable control (e.g. a sample receiving no inhibitor or receiving the inhibitor vehicle only).

Intracellular serotonin levels and/or activity can also be decreased by decreasing NF-κB activity in the cell. NF-κB activity can be decreased, for example, by increasing IκB activity in the cell. IκB activity can be increased, for example, by administering to the cell fluoxetine or other serotonin transporter (5-HTT) inhibitors, as described herein.

Several biochemical tests can provide an index to measure the overall rate of bone remodeling. Biochemical markers are characterized as those related to bone formation or bone resorption. Biochemical markers of bone formation include: serum bone-specific alkaline phosphatase, serum osteocalcin, and serum propeptide of type I procollagen. Biochemical markers of bone resorption include: urine and serum cross-linked N-telopeptide, urine and serum cross-linked C-telopeptide, urine total free deoxypyridinoline, urine hydroxyproline, serum tartrate-resistant acid phosphatase, serum bone sialoprotein, and urine hydroxylysine glycosides. The presence or absence of these markers can be determined by methods known in the art to measure the overall state of bone remodeling at a single point in time. A biochemical marker response to therapy is particularly useful for asymptomatic patients, and biochemical markers can be used to test the effect of a compound on bone mineral density.

Methods of Decreasing Bone Mass

A condition characterized by increased bone mass is a disease or condition in which the subject has increased bone mass compared to a subject who does not have the condition. Increased bone mass can be caused, for example, by excessive bone formation, or by insufficient bone resorption. Examples of conditions characterized by increased bone mass include aging-related hypercalcification. Aging-related hypercalcification shares some features with aging-associated bone diseases with regard to the unphysiological formation of ectopic calcified masses. Examples include the ectopic calcification of soft tissues, such as cartilage and arteries.

Methods of treating a condition characterized by an increase in bone mass in a subject in need thereof involve increasing intracellular levels and/or activity of serotonin. Serotonin levels and/or activity can be increased by administering serotonin or a derivative thereof, a VMAT inhibitor (e.g., reserpine or a reserpine derivative), a MAO inhibitor (e.g., pargylline or derivatives thereof), or a compound or agent that increases the function and/or expression levels of serotonin in the cell. Serotonin levels and/or activity in the cells of the subject can also be increased by increasing NF-κB activity, for example, by decreasing IκB activity.

VMAT inhibitors are naturally-occurring or artificially-derived compounds that inhibit (decrease or prevent) uptake of monoamines within cells. Examples of VMAT inhibitors include reserpine, terazosin, prazosin, methyldopa, guanfacine, guanethidine, guanadrel, guanabenz, doxazosin, clonidine and salts thereof.

MAO inhibitors are naturally-occurring or artificially-derived compound that inhibit (decrease or prevent) the degradation of monoamines, including serotonin, norepinephrine, and dopamine. Examples of MAO inhibitors include pargylline, isocarboxazid, phenelzine, tranylcypromine, and salts thereof.

Modes of Administration

One or more agents can be administered to the subject by an appropriate route, either alone or in combination with another drug. An effective amount of an agent is administered. An effective amount is an amount sufficient to achieve the desired therapeutic or prophylactic effect, under the conditions of administration, such as an amount sufficient to modulate bone mineral density, or osteoclast or osteoblast activation and/or differentiation, and thereby treat an osteopenic condition, inhibit or promote bone resorption, or maintain, increase, or decrease bone mineral density.

The agents can be administered in a single dose or multiple doses. The dosage can be determined by methods known in the art and is dependent, for example, upon the agent chosen, the subject's age, sensitivity and tolerance to drugs, and overall well being. Typically, an effective amount can range from about 0.01 mg per day to about 10 mg per day for an adult. Alternatively, the dosage ranges from about 1 mg per day to about 10 mg per day, from about 10 mg per day to about 100 mg per day, or from about 100 mg per day to about 500 mg per day.

Fluoxetine hydrochloride is typically administered orally. It is chemically unrelated to tricyclic, tetracyclic, or other available antidepressant agents. It is designated ($\pm$)-N-methyl-3-phenyl-3-[($\alpha,\alpha,\alpha$-trifluoro-p-tolyl)-oxy]propylamine hydrochloride and has the empirical formula of $C_{17}H_{18}F_3NO \cdot HCl$.

The SSRIs differ in their pharmacokinetic properties, including half-life. The fluoxetine hydrochloride dosage range for treating depression is 20-80 mg/day or 90 mg/week for delayed release capsules (half-life is 7-9 days). The citalopram hydrobromide dosage range for treating depression is 20-60 mg/day. The fluvoxamine maleate dosage range for treating depression is 50-300 mg/day. The paroxetine hydrochloride dosage range for treating depression is 10-75 mg/day. The sertraline hydrochloride dosage range for treating depression is 50-200 mg/day. The escitalopram oxalate dosage range for treating depression is 10-20 mg/day.

A variety of routes of administration are possible including, but not limited to oral, rectal, intranasal, intraocular, dietary, topical, parenteral (e.g., intravenous, intraarterial, intramuscular, intradermal, intraperitoneal, subcutaneous injection), and inhalation (e.g., intrabronchial, intranasal or oral inhalation, intranasal drops) routes of administration, depending on the agent and disease or condition to be treated.

Another form of administration includes local, in situ administration. Local or in situ administration is carried out by administering the compound directly into a bone, e.g. as an implant, or adjacent to a bone, e.g. subcutaneously (0.05 mm, 0.1 mm, 0.5 mm, 1 mm, 2.5 mm, 5 mm, 7.5 mm, 10 mm, 20 mm from the bone). Moreover, the agents can be incorporated into orthopedic hardware, e.g. bone screws. Pastes or coatings can be applied directly to fractured or injured bones during surgery or applied orally for treatment of periodontitis (e.g. administered directly into, onto, or adjacent to the jaw bone).

Formulation of a therapeutic agent is tailored according to the route of administration selected (e.g., solution, emulsion, capsule). An appropriate composition of the agent to be administered is prepared in a physiologically or pharmaceutically acceptable vehicle or carrier. For solutions or emulsions, suitable carriers include, for example, aqueous or alcoholic/aqueous solutions, emulsions or suspensions, including saline and buffered media.

The precise dose to be employed in the formulation of a therapeutic agent for therapeutic use depends on the route of administration, and the seriousness of the disease or disorder, and should be decided according to the judgment of a practitioner and each patient's circumstances. Effective doses are extrapolated from dose-response curves derived from in vitro or animal model test systems, such as those described herein.

Parenteral vehicles include sodium chloride solution, Ringer's dextrose, dextrose and sodium chloride, lactated Ringer's or fixed oils, for instance. Intravenous vehicles include various additives, preservatives, or fluid, nutrient or electrolyte replenishers and the like (See, generally, Remington's Pharmaceutical Sciences, 17th Edition, Mack Publishing Co., PA, 1985). For inhalation, the agent is solubilized and loaded into a suitable dispenser for administration (e.g., an atomizer, nebulizer or pressurized aerosol dispenser).

Osteoclasts

Elevations in cytoplasmic levels of 5-HT, rather than extracellular levels of 5-HT appear to be responsible for the regulation of osteoclast development. In other systems, although most of the described activities of 5-HT occur via binding to a family of more than 15 receptor subtypes, the results described herein indicate that transporter-mediated events rather than receptor-mediated events are critical to osteoclast development. Because the addition of 5-HT to 5-HT depleted medium, as well as reserpine blockade of intracellular VMAT uptake both increase differentiation, elevations in cytoplasmic levels of 5-HT may be required to enhance NF-κB activation through one or more indirect mechanisms. The finding that reserpine by itself can induce TRAP expression suggests that 5-HT, like TNFα (Azuma et al., 2000, J. Biol. Chem. 275(7):4858-4864), may be able to bypass RANKL signaling.

The invention will be further described by the following non-limiting examples.

EXAMPLE 1

Comparison of Tibiae Density in 5-HTT–/– Mice Compared to Wildtype Mice

Transgenic Swiss Webster mice containing a mutation/disruption of the serotonin transporter (5-HTT) gene (Slc6a4) were prepared. The density of the tibiae bone of wildtype mice and mice that were heterozygous or homozygous for the 5-HTT gene mutation was measured by microCT. Bone volume per total volume (BV/TV) was calculated using techniques known in the art (see, e.g., Muller et al., Bone, 23(1):59-66 (1998)). The BV/TV of the 5-HTT–/– mice was greater than the BV/TV of the wildtype mice. As shown in FIG. 1, homozygote mutant mice, which lack expression of the serotonin transporter, have increased cortical bone density compared to wildtype mice.

EXAMPLE 2

Systemic Fluoxetine Increases Trabecular Parameters

Swiss Webster mice (weighing approximately 25 g; n=9-10) received intraperitoneal injections of fluoxetine (10 mg/kg). The injections were administered once a day (½ life of fluoxetine=1-2 days) for 6 weeks. After 6 weeks the animals were sacrificed and trabecular bones were examined.

Figure 2B:
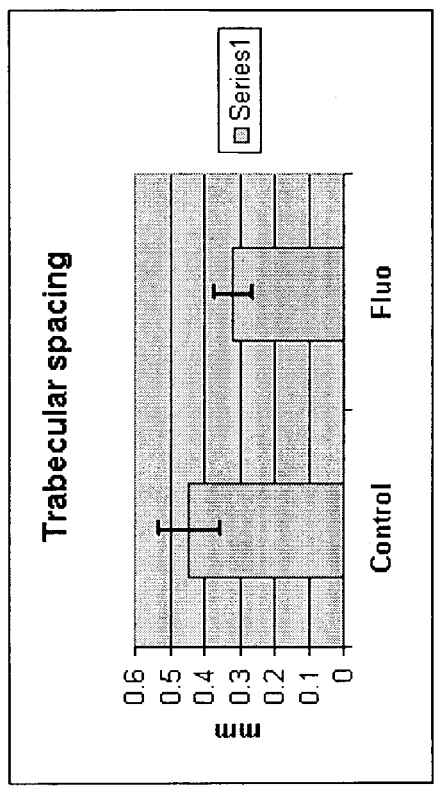
FIG. 2B is a bar graph showing increased trabecular number after treatment with fluoxetine compared to no treatment.
Figure 2C:
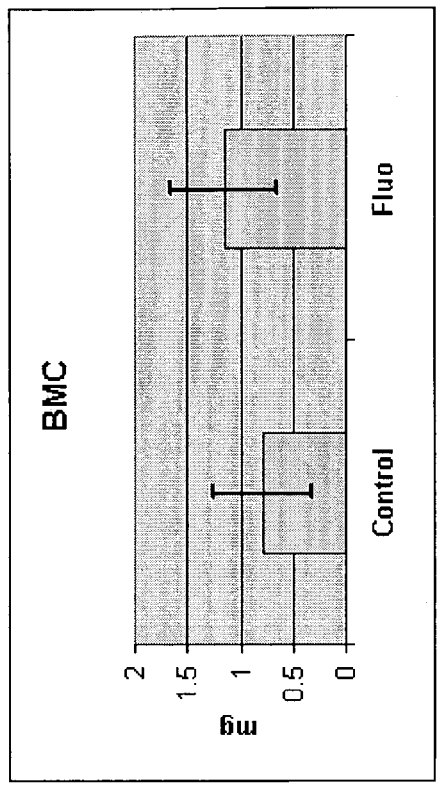
FIG. 2C is a bar graph showing an increase in the connectedness of trabeculae after treatment with fluoxetine compared to no treatment.
Figure 2D:
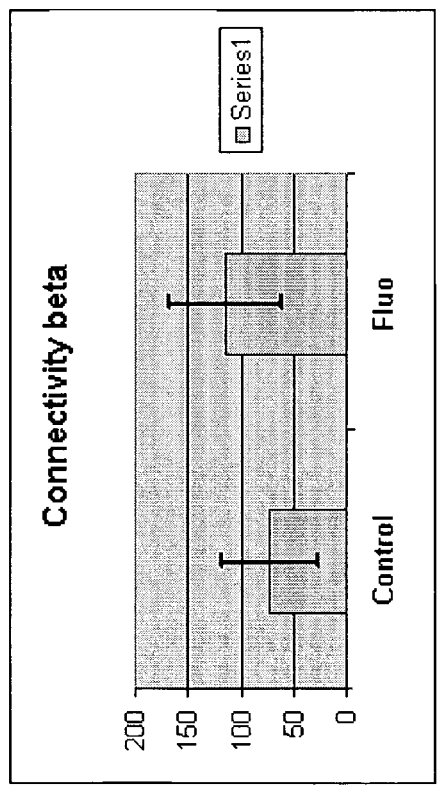
FIG. 2D is a bar graph showing an increase in bone mineral content (BMC) after treatment with fluoxetine compared to no treatment.

The bones of fluoxetine-treated animals had increased mineral content (FIG. 2D). The number of trabeculae per unit length of bone was increased in the fluoxetine-treated mice (FIG. 2B). Moreover, the trabeculae were more connected in the fluoxetine-treated mice (FIG. 2C). There was no significant difference in the thickness of trabeculae between fluoxetine-treated and non-treated mice. Therefore, the trabecular spacing in the fluoxetine-treated mice was decreased as compared to the non-treated mice (FIG. 2A). Thus, systemic treatment of mice with fluoxetine resulted in an increase in trabecular parameters. The increased number, increased connectivity, and decreased space between the transversal structures (i.e. trabeculae) of "spongelike bone" is indicative of increased density and strength of trabecular bone.

EXAMPLE 3

Systemic Fluoxetine and Subcutaneous Injections of Fluoxetine Increase New Bone Formation LPS (50 µl at 5 µg/µl) or PTH was injected subcutaneously above the calvarial bone once on day one to stimulate the osteoclasts. Then, fluoxetine was injected once a day, beginning on day one, for five days. Fluoxetine injections were either intra-calvarial (i.c.) or intra-peritoneal (i.p.). Fluoxetine, 25 µl at 1 mg/ml (3 µM) was injected intra-calvarially (i.c.), whereas 10 mg/kg was injected intra-peritoneally (i.p.). Thus, the mice (body weight of about 25 g) received 25 µg of fluoxetine per day with local, in situ, i.c. injections or 250 µg of fluoxetine per day with systemic, i.p. injections.

After five days, the mice were sacrificed. The calvarium was fixed, decalcified, and analyzed histologically for new bone formation. Van Giesson stain was used to distinguish old bone from new bone (new bone stains blue). FIG. 3 shows the results of examining 7 fields at 20× magnification for the presence of absence of new, i.e. stained bone. The x-axis represents arbitrary units of new bone formation, where 0 represents no new bone and 3 represents high amount of new bone. FIG. 3 shows that subcutaneous, i.e. injection of LPS followed by subcutaneous, i.p. injections of fluoxetine results in increased new bone formation. Similar results were observed in mice receiving an i.e. injection of LPS followed by i.e. injections of fluoxetine. Thus, both local (in situ) administration and systemic administration of fluoxetine stimulate increased new bone formation.

EXAMPLE 4

LPS Alone Stimulates New Bone Formation in 5-HTT Knockout Mice

Wildtype and 5-HTT−/− mice were injected (i.e.) with 50 µl water or 50 µl LPS (5 µg/µl). After one injection, mice were sacrificed. The calvarium was fixed, decalcified, and analyzed histologically for new bone formation using Van Giesson stain.

FIG. 4 shows that wildtype mice (LPS-2) treated with LPS did not exhibit any increased in new bone formation. In contrast, 5-HTT knockout mice (LPS-4) treated with LPS exhibited a significant increase in new bone formation. Injecting 5-HTT knockout mice with LPS alone yields similar results to injecting wildtype mice with LPS and fluoxetine. These results confirm that fluoxetine-inhibition of serotonin uptake by 5-HTT results in increased new bone formation.

EXAMPLE 5

Fluoxetine Increases Bone Nodule Formation in Vitro

Primary osteoblasts obtained from mouse calvaria were cultured in vitro for two weeks. The cells were cultured an additional two weeks in the presence of Vitamin D and the presence or absence of fluoxetine. The cells were then fixed and stained with Von Kossa stain, which stains for calcium phosphate present in bone nodules. Bone nodules formed by osteoblasts in vitro have the same cellular and biochemical composition found in bone. The number of bone nodules were counted. FIG. 5 shows that the number of bone nodules is increased in the presence of fluoxetine.

EXAMPLE 6

Fluoxetine Increases Bone Mass Density in Mice

Eight week old Swiss Webster mice were either untreated, or were treated with fluoxetine (10 mg/kg body weight) by intraperitoneal injection daily for six weeks. The mice were then sacrificed and the femurs were analyzed for alterations in bone mass by microcomputer tomography, using standard tomographic methods. The results of this study are shown in Table 3.

TABLE 3

Effect of Fluoxetine on Bone Mass in Mice

|  | Untreated mice n = 6 | Fluoxetine-treated mice n = 6 |
| --- | --- | --- |
| Trabecular number | 2.44 ± 0.52 | 3.26 ± 0.53 |
| Trabecular spacing | 0.44 ± 0.09 | 0.32 ± 0.05 |
| Trabecular thickness | 0.09 ± 0.01 | 0.09 ± 0.01 |
| Connectedness of trabeculae | 72.8 ± 45.4 | 114.2 ± 53.0 |
| Bone surface (mm$^2$) | 11.4 ± 5.4 | 16.9 ± 7.3 |
| Bone mineral content | 0.79 ± 0.47 | 1.15 ± 0.50 |
| Bone volume/total volume | 11.7 ± 5.2 | 16.7 ± 7.3 |

The results of this study show that mice administered fluoxetine had significant increases in the number of trabeculae, and a reduction in trabecular spacing, with a stable trabecular thickness in the distal femur (FIGS. 10A and 10B). These data indicate an anabolic action with more and new trabeculae, as well as better connected trabeculae, meaning that the bone is better connected and stronger. Overall, there was also a 50% increase in bone volume/total volume, bone surface, and bone mineral content.

EXAMPLE 7

Differentiation of RAW 264.7 and Bone Marrow Cells in Vitro

RAW 264.7 mouse macrophage/monocytes (TIB-71) were purchased from ATCC (Manassas, Va.). Cells were cultured in DMEM/1.5 g/l sodium bicarbonate (JRH Biosciences, Lenexa, Kans.) plus 10% non-heat-inactivated FBS (Invitrogen Corporation Carlsbad, Calif.). When needed, 5-HT was stripped from the FBS by incubating it twice in 0.25% Dextran-coated charcoal (Sigma-Aldrich, St. Louis, Mo.) for 30 minutes at 45° C. Recombinant mouse soluble RANKL (Immunex Corp., Seattle, Wash.) was added at a concentration of 10 ng/ml. Recombinant murine RANKL is an NH2-terminal fusion of a leucine zipper trimerization domain (Fanslow et al., 1994, Semin. Immunol. 6(5):267-278) with residues 134-316 of murine RANKL. When indicated, fluoxetine (Sigma-Aldrich, St. Louis, Mo.) or serotonin receptor antagonists specific for 5-HT1B, 5-HT2B, and 5-HT4 (SB216641, SB204741, CR113808, respectively; Tocris-Cookson, Ellisville, Mo.) were added to the cultures. Cultures were also exposed to the VMAT inhibitor reserpine and the MAO-B inhibitor pargylline (Sigma-Aldrich, St. Louis, Mo.), at the indicated concentrations for 4 days. Mouse bone marrow cells were obtained from long bones of 2-week old C57B1 mice and cultured for 7 days in αMEM/FBS supplemented with 50 ng/ml RANKL and 50 ng/ml human M-CSF (PeproTech Inc., Rocky Hill, N.J.).

5-HT Uptake

To determine 5-HT uptake, RAW 264.7 cells were plated in 48-well plates at a density of $10^4$ cells/well and cultured for 4 days with or without RANKL (10 ng/ml). Cells were washed twice with Hank's Buffered Salt solution (HBSS) and incubated with the indicated concentrations of ($^3$H)5-HT (84 Ci/mmol, Amersham Pharmacia Biotech, Inc. Piscataway, N.J.) in 100 ml HBSS with or without 3 mM fluoxetine for 10 minutes at 37° C. Incubation was terminated with 2 washes of ice-cold HBSS and 1 wash of phosphate-buffered saline (PBS). The accumulated ($^3$H)5-HT was determined by solubilizing the cells with 100 ml 1% SDS and analysis by liquid scintillation spectrometry.

Cytochemical Staining

Cells were stained for tartrate-resistant acid phosphatase (TRAP) using a commercially available kit (#387-A, Sigma-Aldrich, St. Louis, Mo.), according to the manufacturer's directions.

RT-PCR and Northern Blot Analysis

Total RNA was extracted from cells using the TRIAZOL reagent (Invitrogen Corporation, Carlsbad, Calif.), according to the manufacturer's instructions. For RT-PCR, 2 mg of RNA were reversed-transcribed to cDNA using SuperScript II (Invitrogen Corporation, Carlsbad, Calif.) following the manufacturer's instructions. One-tenth of the cDNA was used as a template for the polymerase chain reaction (PCR) 20 (35 cycles at 94° C. for 1 minute, 58° C. for 1 minute and 72° C. for 1 minute). For Northern blot analysis, 10 mg of RNA were size fractionated on a 1.2% agarose denaturing gel and transferred onto nylon membranes. The membranes were hybridized to $^{32}$P radiolabeled probes overnight at 42° C. in hybridization solution (50% formamide, 5× SSC, 5× Denhardt's solution, 0.5% SDS and 100 mg/ml salmon sperm DNA), washed twice to remove unbound probe in 1× SSC, 0.2% SDS at 50° C. for 20 minutes, and exposed to X-ray film. The DNA probes were generated by reverse transcriptase polymerase chain reaction (RT-PCR) from OCL RNA, using the following primer-pairs:

| | | |
|---|---|---|
| 5-htt-a, sense | 5'-GACCAGTGTGGTGAACTGCATGAC-3'; | (SEQ ID NO: 1) |
| antisense | 5'-GATGATGGCAAAGAATGTGGATGCTG-3'; | (SEQ ID NO: 2) |
| 5-htt-b, sense | 5'-ACGTTTGCAGGCCTGGAAGG-3'; | (SEQ ID NO: 3) |
| antisense | 5'-ACACAGCATTCATGCGGATGTCC-3'; | (SEQ ID NO: 4) |
| b-actin, sense | 5'-GAAGAGCTATGAGCTGCCTG-3'; | (SEQ ID NO: 5) |
| antisense | 5'-CACAGAGTACTTGCGCTCAG-3'; | (SEQ ID NO: 6) |
| trap, sense | 5'-ACACAGTGATGCTGTGTGGCAACTC-3'; | (SEQ ID NO: 7) |
| antisense | 5'-CCAGAGGCTTCCACATATATGATGG-3'; | (SEQ ID NO: 8) |
| cathepsin K, sense | 5'-CTGAAGATGCTTTCCCATATGTGGG-3'; | (SEQ ID NO: 9) |
| antisense | 5'-GCAGGCGTTGTTCTTATTCCGAGC-3'; | (SEQ ID NO: 10) |
| c-src, sense | 5'-TCCAGGCTGAGGAGTGGTACTTTGG-3'; | (SEQ ID NO: 11) |
| antisense | 5'-ATACGGTAGTGAGGCGGTGACACAG-3'; | (SEQ ID NO: 12) |
| MMP-9, sense and | 5'-CGAGTGGACGCGACCGTAGTTGG-3'; | (SEQ ID NO: 13) |
| antisense | 5'-CAGGCTTAGAGCCACGACCATACAG-3'; | (SEQ ID NO: 14) |

Probe sequences were confirmed by sequencing.

Immunochemical Staining

Undifferentiated and differentiated RAW 264.7 cells were stained using an anti-5-HTT monoclonal antibody (CHEMICON International, Inc. Temecula, Calif.).

Isolation of Nuclear Proteins

Cells were pelleted, washed twice with PBS and resuspended in 800 ml ice-cold lysis buffer (HEPES 10 mM; KCl 10 mM; EDTA 0.1 mM; EGTA 0.1 mM; DTT 1.0 mM; PMSF 1.0 mM; aprotinin 10 mg/ml, pepstatin 10 mg/ml, leupeptin 10 mg/ml). The samples were incubated on ice for 30 minutes, vortexed for 30 seconds after addition of 50 ml of 10% Nonidet-P40, and then centrifuged for 10 minutes at 4° C. The pellets were resuspended in an ice-cold nuclear buffer (HEPES 20 mM; NaCl 400 mM; EDTA 1.0 mM; EGTA 1.0 mM; DTT 1.0 mM; PMSF 1.0 mM; aprotinin 10 mg/ml, pepstatin 10 mg/ml; leupeptin 10 mg/ml), incubated on ice for 2 h, and centrifuged for 10 minutes at 4° C. The supernatants were collected as nuclear extract and stored at −70° C. Protein concentration was determined using the Pierce protein assay reagent (Pierce, Rockford, Ill.), according to the manufacturer's instructions.

Electrophoretic Mobility Shift Assay

Double stranded oligonucleotides (5'-AGTTGAGGG-GATTTCCCAGGC-3' (SEQ ID NO: 15), 3'-TCAACTC-CCCTGAAAGGGTCCG-5' (SEQ ID NO: 16)) were end labeled with $^{32}$[P]-ATP and incubated with the nuclear extract for 20 minutes at room temperature. The samples were loaded on a 4% non-denaturing polyacrylamide gel. The gel was then dried and exposed to X-ray film. For competition experiments, nuclear extracts were incubated with unlabeled double-stranded NF-κB or AP-1 oligonucleotides for 20 minutes. Labeled oligonucleotides were then added to the reaction mixture. For supershift assays, nuclear extracts were incubated with either p65 or p50 antibodies (Santa Cruz Biotechnology, Santa Cruz, Calif.) overnight at 4° C. followed by the addition of the labeled oligonucleotides.

EXAMPLE 8

Osteoclasts Express a Functional 5-HTT

Gene microarrays were used to determine if developing osteoclasts express serotonergic molecules. Osteoclasts were generated by stimulating murine RAW 264.7 macrophage-like cells with RANKL (Battaglino et al., 2002, J. Bone Miner. Res. 17(5) 763-773). After four days in culture, numerous multinucleated giant cells (>5 nuclei) formed (Battaglino, supra). These cells strongly expressed all osteoclast-specific markers including tartrate-resistant acid phosphatase (TRAP), cathepsin K, calcitonin receptor, matrix metalloprotease-9 (MMP-9), c-src and the proton pump subunit ATP6I, and formed resorption pits on bone slices and sub-micron calcium phosphate films (Battaglino, supra). mRNA from RANKL-induced osteoclasts or unstimulated RAW 264.7 cells was reversed transcribed to cDNA, and used to probe gene microarrays, using methods known to one skilled in the art. The sodium-dependent serotonin transporter (5-HTT) was strongly upregulated in RANKL-induced cells, compared to unstimulated cells (FIGS. 6A and 6B). This result was confirmed by RT-PCR (FIG. 6C), Northern blot analysis (FIG. 6D), and immunohistochemistry (FIGS. 6E and 6F) of differentiated osteoclasts compared to undifferentiated RAW 264.7 cells.

To determine if the osteoclast-expressed 5-HTT was functional, 5-HT uptake assays were performed. Differentiated osteoclasts transported 5-HT in a concentration-dependent manner, indicating that the 5-HTT can be saturated (FIG. 7A). Uptake of 5-HT was completely blocked by the SSRI fluoxetine. Kinetic studies revealed that 5-HT uptake activity could be seen as early as 24 hours after RANKL stimulation (FIG. 7B).

EXAMPLE 9

5-HTT Blockade Inhibits Osteoclast Formation

The differential expression of a functional 5-HTT in osteoclasts suggested that 5-HT transport could play a role in osteoclast differentiation. Fluoxetine inhibited the formation of TRAP positive cells in a dose-dependent manner (FIG. 7C), whereas unstimulated RAW 264.7 proliferation was unaffected, indicating a lack of toxicity. Northern blot analysis of parallel cultures showed a significant reduction in the expression of the late osteoclast markers cathepsin K (FIG. 7E) and MMP-9 (FIG. 7F) in fluoxetine-treated cells (~70% and 80%, respectively), whereas a smaller effect was seen on the expression of an early marker, TRAP (~20%) (FIG. 7D). To confirm this finding in normal cells, osteoclasts from normal mouse bone marrow cells (BMC) were generated in the presence of M-CSF and RANKL. BMC-derived osteoclasts expressed the above-described panel of osteoclast specific markers, and also strongly expressed 5-HTT mRNA. Fluoxetine also significantly inhibited BMC-derived osteoclasts (FIG. 7G).

EXAMPLE 10

5-HT Stimulates Osteoclast Formation

The requirement for intact 5-HTT function suggested that 5-HT is needed and must be transported into the cell for normal osteoclast differentiation to occur. The 10% fetal bovine serum supplemented medium used to support cultures contained high levels of serotonin from platelet lysis (300 ng/ml by ELISA). The addition of serotonin (3-300 ng/ml) had no effect on osteoclast formation in cultures containing FBS. When 5-HT was depleted approximately 80-fold from FBS by two cycles of adsorption to dextran-activated charcoal, RANKL-stimulated RAW 264.7 cells still generated osteoclasts, albeit in lower numbers than in 5-HT replete serum (e.g., FIG. 8A, solid bars). However, the number of osteoclasts was significantly increased by added serotonin at either 30 or 300 ng/ml, and the osteoclast markers cathepsin K and MMP-9 were both up-regulated (FIGS. 8B and 8C, respectively).

EXAMPLE 11

5-HT Receptor Blockade Does Not Affect Osteoclast Formation

In addition to the 5-HTT, RAW 264.7-derived osteoclasts expressed mRNA transcripts for 5-HT receptors 5-HT1B, 5-HT2B and 5-HT4 (FIG. 8D). Serotonin could therefore modulate osteoclast differentiation and activation through either the 5-HTT, 5-HT receptors, or both. To distinguish among these possibilities, osteoclast differentiation was assessed in the absence/presence of fluoxetine and a mixture of receptor antagonists specific for 5-HT1B, 5-HT2B and 5-HT4, respectively. Fluoxetine suppressed osteoclast differentiation in both 5-HT replete (FBS) and depleted (FBS−) serum (FIG. 8A). In contrast, the combination of 5-HT receptor antagonists (FIG. 8A; Antag) had no positive or negative effect on differentiation, and the mixture of 5-HT antagonists plus fluoxetine (FIG. 8A; Antag/Fluo) showed equivalent inhibition to fluoxetine alone. Thus, the 5-HTT, rather than cell surface receptor-mediated activities, appears to be the primary modulator of osteoclast differentiation in this system.

EXAMPLE 12

Reserpine Stimulates Osteoclast Multinucleation

In neurons, 5-HT taken up via the 5-HTT is either degraded by monoamine oxidase (MAO) or sequestered in intracellular vesicles, the latter action mediated by a vesicular monoamine transporter (VMAT). Reserpine, a VMAT inhibitor, promoted osteoclast differentiation in the presence of RANKL, whereas pargylline (MAO-B inhibitor) had no effect (FIG. 8E). In addition to increasing osteoblast numbers, reserpine treatment also stimulated the formation of much larger cells with greater multinucleation that covered the entire culture dish. Reserpine treatment in the absence of RANKL induced TRAP expression by a number of mono- and bi-nucleated cells (FIG. 8F), although large multinucle- ated osteoclasts were not formed. These data indicate that elevated intracellular 5-HT levels synergize with RANKL- induced signals, and may by themselves have a limited ability to induce the expression of early osteoclastic genes in a RANKL-independent manner.

EXAMPLE 13

Fluoxetine Inhibits NF-κB Activation

Activation of the transcription factor NF-κB is stimulated by RANKL and is essential for osteoclast formation (Udagawa et al., 1999, Bone 25(5):517-523). The inhibition of differentiation by blocking the 5-HTT could be due, in part, to an inhibition of NF-κB activation. To test this hypothesis, electrophoretic mobility shift assays (EMSA) were performed, as described herein. RANKL induced a 20-fold increase in NF-κB activation compared to unstimulated RAW 264.7 cells (FIG. 9A). In cells treated with RANKL and fluoxetine, activation was inhibited by 80%. Addition of a 100-fold excess cold NF-κB oligodeoxynucleotide (ODN) blocked binding, but an unrelated (AP-1) ODN had no effect on it. Supershift assays revealed that the NF-κB band was retarded by an anti-p65 antibody, but not by an anti-p50 antibody (FIG. 9B). In fluoxetine-treated RANKL-stimulated cells, levels of the inhibitor IκBA were elevated compared to cells without fluoxetine by Western analysis, and were similar to the levels seen in unstimulated cells (FIG. 9C). The reduction in intracellular 5-HT following fluoxetine treatment could therefore impinge on pathways that regulate IκB, for example, IκBA phosphorylation and degradation.

EXAMPLE 14

Methods for Detecting and/or Identifying Agents that Modulate Bone Remodelling

Methods for detecting and/or identifying an agent or compound (candidate modulator, test modulator, test agent, candidate agent, candidate compound, or test compound) to be tested that increases activation and/or differentiation of osteoblasts are also described herein. Osteoblasts are contacted with a candidate compound and the levels and/or activity of serotonin in the cell is measured. A candidate compound that decreases expression of the levels and/or activity of serotonin in an osteoblast relative to a control is a compound that modulates bone remodelling. Such methods may be carried out in a subject, for example, a mammal, such as a mouse or a human, or the methods may be carried out using an ex vivo system, for example, cultured cells (e.g., RAW 264.7 cells stimulated with RANKL as described herein) or primary cells.

As used herein, a "candidate modulator," "test modulator," "candidate compound," "test compound," "test agent," "candidate agent," or "agent to be tested" is a molecule, be it naturally-occurring or artificially-derived, and includes, for example, peptides, proteins, peptidomimetics, synthetic molecules (for example, synthetic organic molecules) naturally-occurring molecules (for example, naturally occurring organic molecules), nucleic acid molecules, and components thereof.

In general, test agents for use in the present invention may be identified from libraries of natural products or synthetic (or semi-synthetic) extracts or chemical libraries according to methods known in the art. The precise source of test extracts or compounds is not critical to the screening procedure(s) of the invention. Accordingly, virtually any number of chemical extracts or compounds can be screened using the exemplary methods described herein. Examples of such extracts or compounds include, but are not limited to plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic small molecule libraries are commercially available, e.g., from ChemBridge Corporation (San Diego, Calif.), Brandon Associates (Merrimack, N.H.), and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

An inhibitor of serotonin function or an SSRI can decrease serotonin function/activity in varying degrees. For example, the inhibitor can decrease serotonin function/ activity by at least about 10%, 40%, 50%, or 75%, or by at least about 90%, relative to an appropriate control.

Promoters of serotonin function can also be identified according to the methods described herein. As used herein, a "promoter" is an agent which increases (induces or enhances) or activates at least one function characteristic of serotonin. The term promoter includes agents that bind serotonin and activate or increase function, and agents that increase or activate a function of serotonin without binding thereto. Preferably, the promoter increases or activates or enhances serotonin function by at least about 10%, 25%, 50%, 60%, 70%, 10%, 80% 90% or 100% compared to a suitable control (e.g., a sample receiving no promoter or receiving the promoter vehicle only). Promoters of serotonin function include VMAT inhibitors, for example, reserpine and salts or derivatives thereof, and MAO inhibitors, for example pargylline, isocarboxazid, phenelzine, tranylcypromine, and salts or derivatives thereof. Agents that increase serotonin levels or activity in the cell are promoters of serotonin function.

One example for detecting and/or identifying an inhibitor or promoter of serotonin function as described above, is to measure osteoclast differentiation or activation. This can be done, for example, by stimulating RAW 264.7 mouse macrophage cells with RANKL, as described herein, in the presence or absence of the test agent. Differentiated osteoblasts express the following markers: tartrate-resistant acid phosphatase (TRAP), cathepsin K, and matrix metalloprotease-9 (MMP-9). Thus increased expression (assessed, for example, by Western blot analysis, Northern blot analysis, immunocytochemistry, quantitative reverse transcriptase-polymeraase chain reaction techniques, or other standard expression analysis techniques) of one or more of these markers by a test agent, indicates that the test agent induces activation or differentiation of osteoclasts. Conversely, decreased expression of one or more of these markers by a test agent, indicates that the test agent inhibits activation or differentiation of osteoclasts.

Depending on the function of the inhibitor, another method for detecting inhibitors or promoters of serotonin function is to measure uptake of serotonin by cells. Test agents that modulate the uptake of serotonin can be detected and/or identified using this method.

Yet another assay for detecting activation and/or differentiation of osteoclasts is measuring the activity of NF-κB and/or IκB in the osteoclasts. Measurements of such activities can be done using methods known in the art. In osteoclasts, increased NF-κB activity and/or decreased IκB activity indicates activation or increased activation and/or differentiation or increased differentiation of the osteoclasts, while decreased NF-κB activity and/or increased IκB activity indicates decreased activation and/or differentiation of the osteoclasts.

Another assay for identifying modulators of bone remodelling involves molecular modeling techniques to identify compounds that are structurally related to the compounds described herein (e.g., SSRIs) but which are chemically distinct. Such methods can be carried out using computer programs that allow for the testing of a library of compounds for functional activity that is similar to that of the reference compound. Test compounds that are identified as having similar functional activity to the reference compound can then be tested in an in vitro or in vivo assay.

This invention further pertains to novel compounds identified by the screening assays and use of such compounds in therapy, for example, for modulating bone remodeling, modulating bone mineral density, treating an osteopenic condition, or increasing or decreasing activation or differentiation of osteoclasts or osteoblasts. A compound identified as described herein (e.g., a test agent that is an inhibitor of serotonin function, such as an antibody, a polypeptide, or a small molecule inhibitor) can be further assessed in an appropriate animal model to determine the efficacy, toxicity, or side effects of treatment with such a compound.

All references cited herein are incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method of stimulating bone formation, comprising
(a) identifying a subject characterized as suffering from or at risk of developing an osteopenic condition; and
(b) contacting an osteoblast of said subject with a serotonin reuptake inhibitor, wherein bone formation is increased in the presence of said inhibitor compared to in its absence, and wherein said serotonin reuptake inhibitor is fluoxetine or fluoxetine hydrochloride.

2. The method of claim 1, wherein the bone mass density value of said subject is at least one standard deviation below a reference bone mass density value of an age-matched individual or index.

3. The method of claim 1, wherein said osteopenic condition or risk of developing said condition is diagnosed by a technique selected from the group consisting of x-ray, dual energy x-ray absorptiometry (DEXA), single energy x-ray absorptiometry (SXA), ultrasound, quantitative computed tomography (QCT), and magnetic resonance.

4. The method of claim 1, wherein cortical bone mass of said subject is increased following contact of said osteoblast with serotonin reuptake inhibitor.

5. The method of claim 1, wherein trabecular bone mass of said subject is increased following contact of said osteoblast with said serotonin reuptake inhibitor.

* * * * *